June 14, 1955 G. T. CHAFFIN Plant Pat. 1,399
PECAN TREE
Filed Feb. 23, 1954
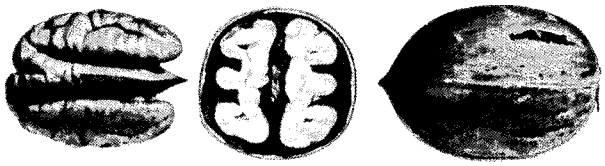
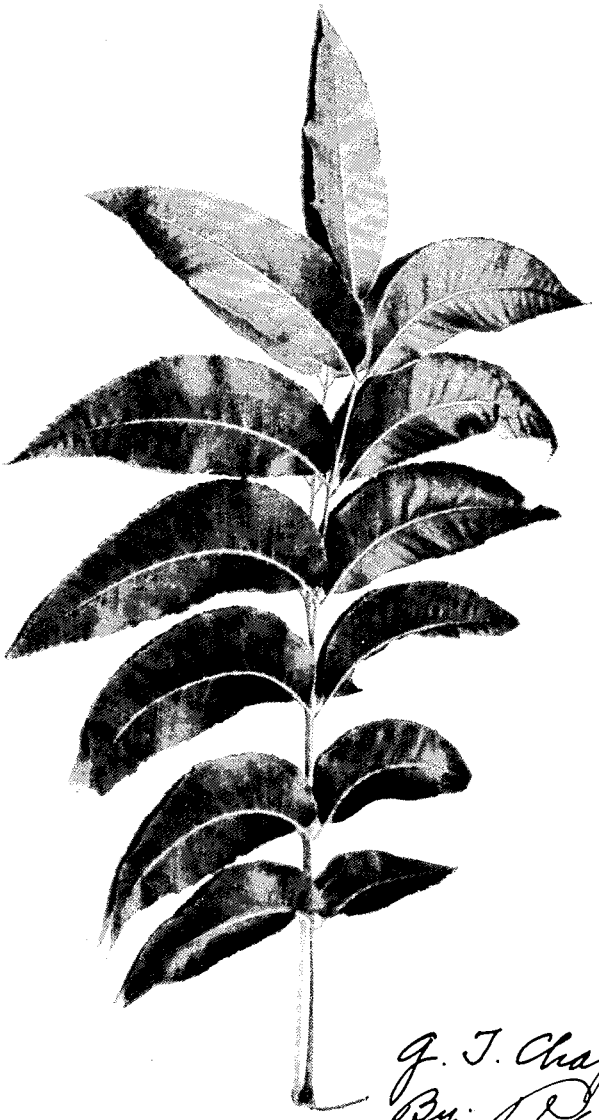
INVENTOR
G. T. Chaffin
By: Robert Cobb
ATTORNEYS.

United States Patent Office

Plant Pat. 1,399
Patented June 14, 1955

1,399

PECAN TREE

Gordon T. Chaffin, Monticello, Ga., assignor to H. G. Hastings Co., Atlanta, Ga., a corporation of Georgia Application February 23, 1954, Serial No. 412,142

1 Claim. (Cl. 47—62)

The present invention relates to a new and distinct variety of pecan tree which was originated from a cultivated seed of the "Stuart" pecan variety (unpatented). The new variety generally resembles the "Stuart" variety, but is definitely distinguished therefrom by the fact the nuts of the new variety have a much thinner shell, averaging about .015 to .020 inch in thickness as compared with the thickness of the shell of the nuts of the "Stuart" variety which average about .040 to .042 inch in thickness.

Because of the extreme thinness of the nut shells of my new variety, it is especially suited for commercial use because of the ease with which the nuts may be cracked, and the ease with which the nut meats can be extracted without breaking the meats. This attribute is very important from a commercial standpoint, since whole nut meats command much higher market prices.

The nuts of my new variety fill out very well and the meat is of excellent quality, said nuts being at least equal to the normal size and quality of the "Stuart" variety, while at the same time, being resistant to scab and other common diseases to which most pecan varieties are subject.

Asexual reproduction of my new variety by both grafting and budding, as performed in Jefferson County, Florida, shows that the foregoing characteristics and distinctions come true to form and are established and transmitted through succeeding propagations.

The accompanying drawing shows typical specimens of the nuts of my new variety, as well as a typical specimen branch depicting the foilage thereof, the views of the nut specimens including a view in side elevation depicting the exterior characteristics of the nuts, a view in transverse cross-section depicting the extreme thinness of the shell and the plump meats within the shell, and a view in elevation of one of the meats as removed in whole from the shell.

The following is a detailed description of my new variety, with color terminology in accordance with general color terms of ordinary dictionary significance, said description being based upon specimens grown and observed in a nut grove near Monticello, Jasper County, Georgia:

Dates first and last picking—About October 1st to about November 1st.

Tree: Medium size; vigorous; hardy.

*Productivity.*—Very productive.
*Growth Habit.*—Vigorous. Limbs—heavy.
*Foliage.*—Abundant.
*Buds.*—Long-pointed; similar to "Stuart" variety. Color—brown.

Nuts:

*Ripening.*—Even.
*Time of harvest.*—October.
*Quantity.*—Abundant.
*Maturity.*—Medium.
*Tenacity.*—Free.
*Cluster.*—Number—average 3 or 4 nuts per cluster. Size—Medium-large.
*Size.*—Length from 1¼ to 1½ inches; diameter about ¾ inch.
*Weight.*—Average number of nuts per pound—from 60 to 75.
*Shape.*—Base—round. Point—mucronate.
*Shell.*—Extremely thin; shell thickness from .015 to .020 inch; cracks and releases exceedingly easily.
*Color.*—Brown, with black pencilling mostly toward tip.
*Kernel.*—Flavor—good. Shape—very slightly tapering toward tip. Texture—firm. Sutures—even.

Disease resistance: Has not contracted diseases, particularly pecan scab, as determined from comparison with other varieties, including "Schley" (unpatented), grown under comparable cultural conditions in Jasper County, Georgia.

I claim:

A new and distinct variety of pecan tree, substantially as herein shown and described, characterized particularly as to novelty by the extreme thinness and easy-cracking qualities of its nut shells, by the plumpness and excellent quality of its nut meats, and by its good resistance to pecan scab.

No references cited.